(12) United States Patent
Wisdom et al.

(10) Patent No.: US 8,598,386 B2
(45) Date of Patent: Dec. 3, 2013

(54) PROCESS FOR PRODUCING LACOSAMIDE

(75) Inventors: Richard Wisdom, Eppstein (DE); Joerg Jung, Floersheim (DE); Andreas Meudt, Weisbaden (DE)

(73) Assignee: Euticals GmbH, Frankfurt am Main (DE)

( * ) Notice: Subject to any disclaimer, the term of this patent is extended or adjusted under 35 U.S.C. 154(b) by 224 days.

(21) Appl. No.: 13/274,718

(22) Filed: Oct. 17, 2011

(65) Prior Publication Data

US 2012/0095251 A1    Apr. 19, 2012

(30) Foreign Application Priority Data

Oct. 19, 2010 (EP) .................................. 10188079

(51) Int. Cl.
*C07C 231/02* (2006.01)
*C07C 231/12* (2006.01)
*C07C 231/14* (2006.01)
*C07C 269/06* (2006.01)

(52) U.S. Cl.
USPC .............................. 564/158; 564/164; 560/29

(58) Field of Classification Search
USPC ..................... 564/158, 164; 560/29
See application file for complete search history.

(56) References Cited

U.S. PATENT DOCUMENTS

| | | | |
|---|---|---|---|
| 5,773,475 A | 6/1998 | Kohn | |
| 6,048,899 A | 4/2000 | Kohn et al. | |
| 7,884,134 B2 * | 2/2011 | Riedner et al. | 514/616 |

FOREIGN PATENT DOCUMENTS

| | | |
|---|---|---|
| EP | 2067765 A2 | 6/2009 |
| WO | WO 9733861 A1 | 9/1997 |
| WO | WO 2006037574 A1 | 4/2006 |
| WO | WO 2010052011 A1 | 5/2010 |
| WO | WO 2010107993 A1 | 9/2010 |

OTHER PUBLICATIONS

Choi, D. et al., "Synthesis and Anticonvulsant Activities of N-Benzyl-2-acetamidopropionamide Derivatives" *J.Med.Chem.*, 39 (1996) pp. 1907-1916.

Andurkar S.V. et al., "Synthesis and Anticonvulsant Activities of (R)-(0)-methylserine Derivatives" *Tetrahedron Asymmetry*, 9 (1998) pp. 3841-3854.

* cited by examiner

*Primary Examiner* — Shailendra Kumar
(74) *Attorney, Agent, or Firm* — ProPat, L.L.C.

(57) ABSTRACT

The present invention relates to a method for producing (R)-2-acetamido-N-benzyl-3-methoxypropionamide (lacosamide), by methylation of (R)-2-acetamino-2-N-benzyl-3-hydroxy-propionamide (V), in which the methylation is carried out at a temperature below 20° C.

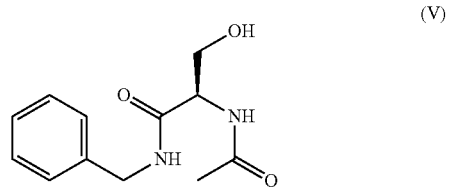

(V)

11 Claims, 4 Drawing Sheets

PROCESS FOR PRODUCING LACOSAMIDE

CROSS-REFERENCE TO RELATED APPLICATIONS

This application claims priority to European Patent Application 100188079.7-2117 filed Oct. 19, 2010 which is hereby incorporated herein by reference in its entirety.

FIELD OF THE INVENTION

The present invention relates to a method for producing (R)-2-acetamido-N-benzyl-3-methoxypropionamide (lacosamide).

BACKGROUND OF THE INVENTION (R)-2-Acetamido-N-benzyl-3-methoxypropionamide, also known as lacosamide, is effective in the treatment of pain, osteoarthritis, migraine and epilepsy. Lacosamide has the structure given below (I)

(I)

Structure of Lacosamide

The product is described and claimed in WO9733861. This document describes different synthetic methods. Starting with (D)-serine, this amino acid is converted to (R)-2-acetamino-2-N-benzyl-3-hydroxy-propionamide by coupling with benzylamine (BnNH2) followed by acetylation using acetic anhydride (Ac$_2$O). This is then methylated using methyl iodide (MeI) and silver oxide (Ag$_2$O) to produce the required product (Scheme 1).

Scheme 1: Method for preparation of Lacosamide given in WO9733861

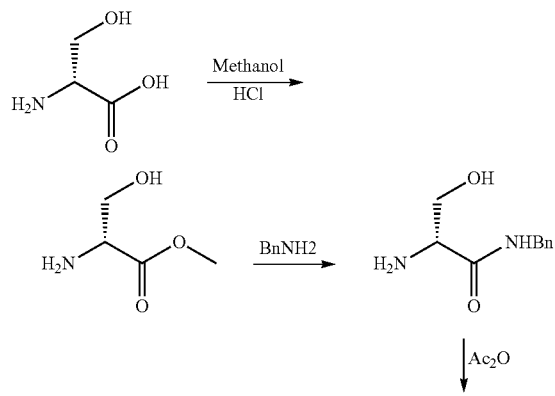

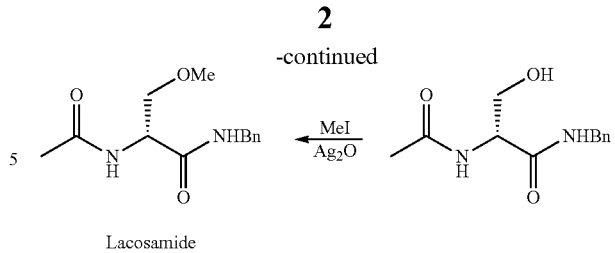

Lacosamide

Alternatively, (D)-serine is first acetylated, the resulting N-acetyl amino acid coupled with benzylamine, under conditions described in Journal of the American Chemical Society (1967), 89, pp 5012-7 via a mixed anhydride, and finally methylated with a combination of methyl iodide and silver oxide (Scheme 2). In both cases the intermediates are difficult to isolate from the reaction solutions and are difficult to handle.

Scheme 2:
Alternative method for preparation of Lacosamide given in WO9733861

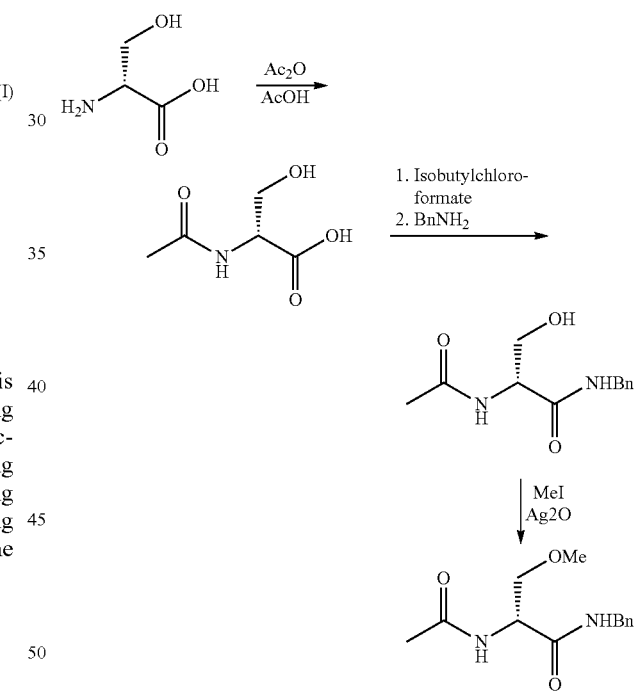

In a further alternative approach to prepare lacosamide described in WO9733861, the amino group of (D)-serine is first protected with a protecting group, such as a carboxybenzyl-group (Cbz). This is followed by 'O'-methylation and subsequent reactions to the desired product, eg benzylamination at the carboxylic acid function, de-protection, and acetylation of the amine function (Scheme 3). This route is also described in U.S. Pat. No. 6,048,899; which additionally provides a similar approach with inversion of steps 2 and 3, i. e. the amide formation is performed prior to the methylation.

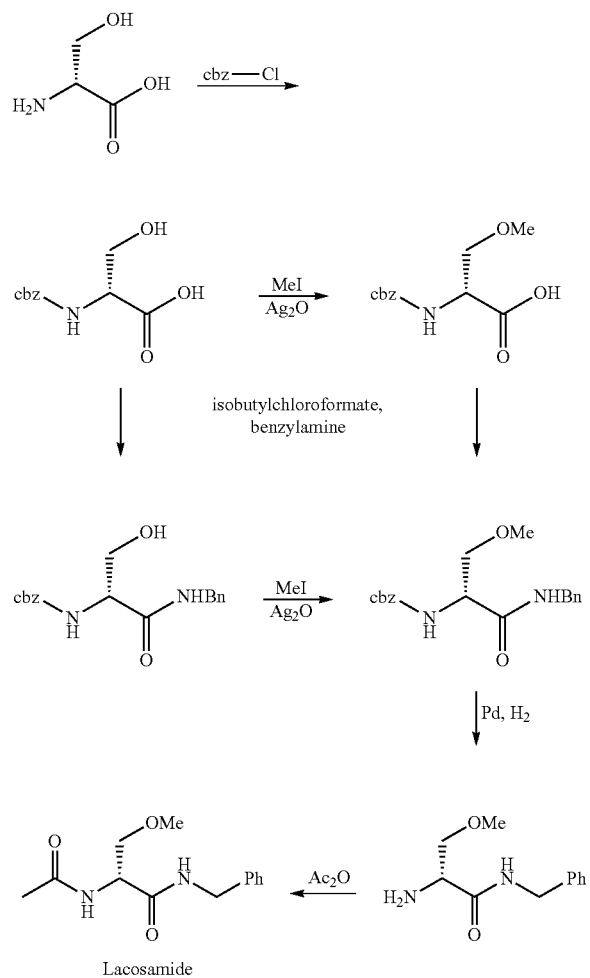

Scheme 3:
Further alternative method for preparation of Lacosamide given in WO9733861 (whose United States equivalents are U.S. Pat. Nos. 5,773,457; 6,048,899, and US RE 38551) and US6048899.

Lacosamide

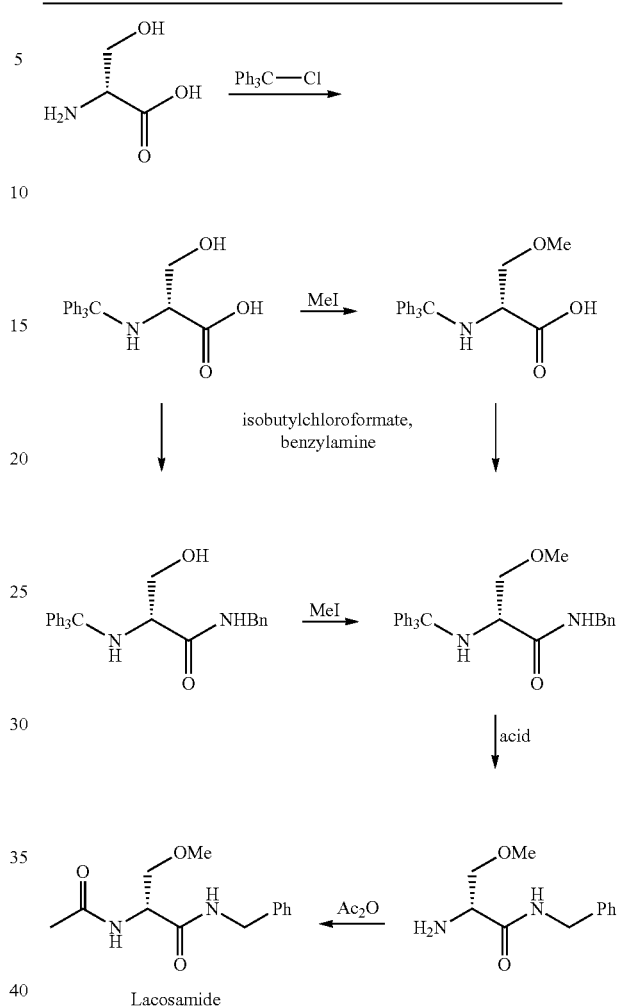

Scheme 4: Method for production of Lacosamide in EP2067765 A1

Lacosamide

However, all those processes suffer from use of large quantities of silver, which is both expensive and must be removed from the final product. Additionally partial racemisation of the expensive chiral centre is observed in several cases, which lowers yields. Recently WO2010107993 (whose United States equivalent is United States Patent Publication No. 2010/240926A1) has been published. This describes a similar route to that in Scheme 3 except that (R)-N-benzyl-2-(benzyloxycarbonylamino)-3-hydroxy-propionamide is methylated using dimethyl sulfate at temperatures between −15° C. and 25° C. By operating at lower temperatures it is claimed that undesired methylation at the nitrogen groups is reduced.

A further process for the production of lacosamide has also been described in EP2067765 A1 (whose United States equivalent is United States Patent Publication No. 2009/143472A1). This uses the very bulky trityl-protecting group for protection of the serine, thereby minimising the potential for racemisation at the chiral centre during the subsequent methylation reaction (Scheme 4).

Although the use of expensive silver oxide is no longer necessary using trityl as protecting group, the necessity to perform many transformations on "tritylated" materials, with a very high molecular mass, makes the process less effective from an economic point of view.

Alternatively WO 2006037574 (whose United States equivalents are United States Patent Publication Nos. 2008/027137A1 and 2011/1303350A1) also describes a process for lacosamide production starting from (D)-serine. In this process, the amine group is protected with a boc (tert-butoxycarbonyl-) group, and the methylation of the boc protected amino acid is carried out in the presence either of a phase transfer catalyst plus base or an organolithium reagent. After methylation, the boc protected (D)-methoxy-serine is worked through to the lacosamide via benzylamination, de-protection, and acetylation.

Recently WO2010052011 has been published which describes routes to racemic lacosamide (a mixture of (R)- plus (S)-2-acetamido-N-benzyl-3-methoxypropionamide). The racemic mixture is then separated using simulated bed chromatography (SMB) with a chiral phase, and the unwanted enantiomer is then racemised and recycled (Scheme 5).

Scheme 5: Method for production of Lacosamide in WO2010052011

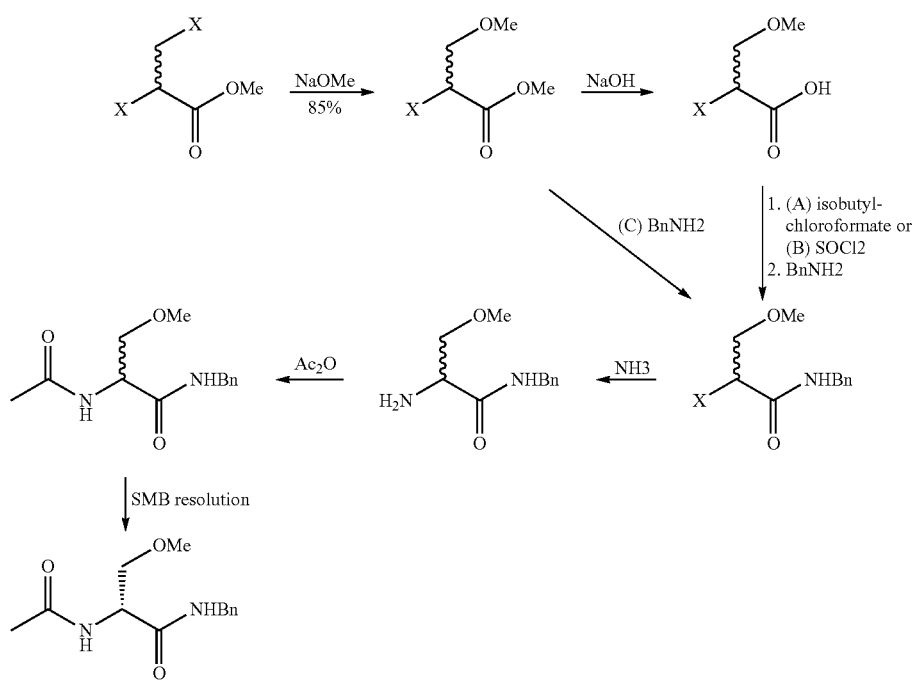

SUMMARY OF ADVANTAGEOUS OBJECTS OF THE INVENTION

Despite these various approaches, there still remains a need for improved processes for the production of this important drug.

DETAILED DESCRIPTION OF ADVANTAGEOUS EMBODIMENTS OF THE INVENTION

Figure 1:
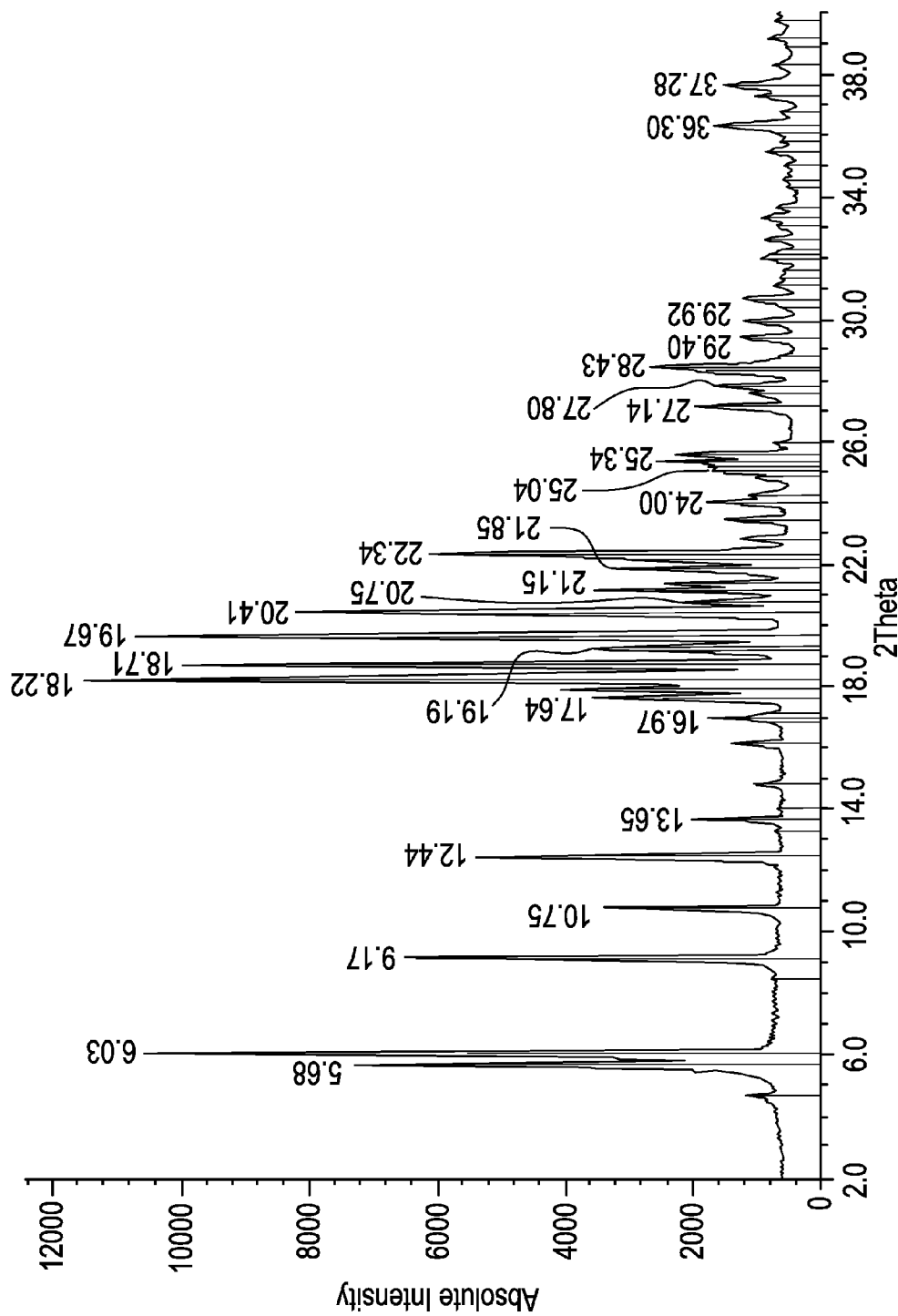
FIG. 1 is an X-ray diffraction pattern of exemplary isolated crystals of (R)-boc-2-amino-N-benzyl-3-hydroxy-propionamide (III) formed in accordance with Example 2.

It is the purpose of the invention to provide for an improved method of methylation of the intermediate (R)-2-acetamino-2-N-benzyl-3-hydroxy-propionamide (compound (V) in Scheme 6 below) to produce (R)-2-acetamino-2-N-benzyl-3-methoxy-propionamide (lacosamide).

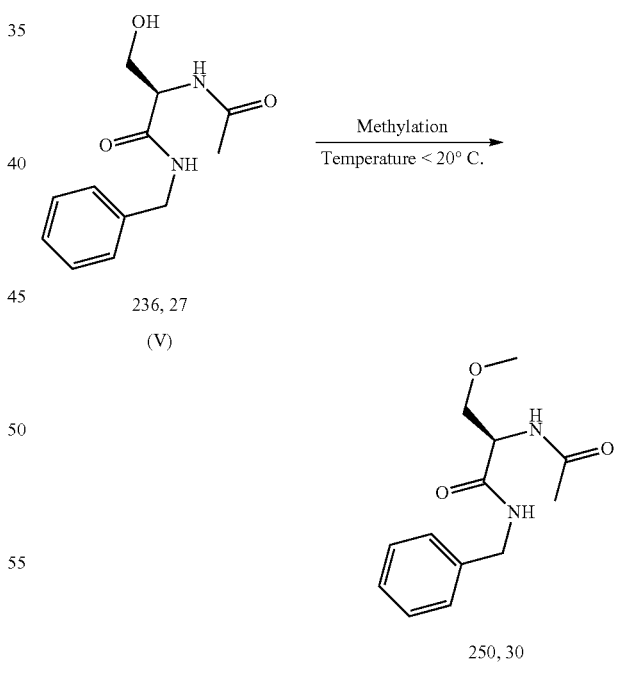

Scheme 6:
Method for production of Lacosamide according to this Invention

Methylation of (R)-2-acetamino-2-N-benzyl-3-hydroxy-propionamide (V) under normal conditions to produce lacosamide typically results in significant racemisation at the chiral centre. In WO9733861, silver oxide is added to minimise racemisation, however this is expensive and results in the need to remove large qualities of silver. Whilst it is possible to obtain lacosamide with an ee of greater than 99% from less enantiomerically pure lacosamide (eg with an ee of 90%) by crystallisation, this results in considerable yield loss. It is therefore preferable to minimise racemisation. Surprisingly it is found that under cold conditions (preferably below 10° C.), racemisation is greatly reduced, whilst the reaction still proceeds at a suitable rate for economic production. Racemisation can therefore be minimised while still maintaining good methylation activity by reducing the temperature below 20° C. or more preferably below 10° C. or even more preferably below 5° C. In this way it is economically practical to carry out methylation directly on the intermediate (R)-2-acetamino-2-N-benzyl-3-hydroxy-propionamide (V) without the need for a bulky protecting group (eg benzyloxycarbonyl- or trityl-) at the amine to reduce racemisation or without the need for addition of large quantities of silver oxide which is both expensive and difficult to remove to trace levels. Although WO2010107993 claims the use temperatures below 25° C. during methylation, the invention described here is very different. WO2010107993 describes methylation of a carbamate compound, whereas methylation of an amide is described in the current invention. These 2 groups would be expected to have very different effects on the stability of the chiral centre and the reactivity at the nitrogen. In WO2010107993, the reduced temperature during methylation leads to a reduction in undesired methylation at the nitrogen group. The effect on racemisation is not described and indeed is most likely not an issue at higher temperatures (such as 25° C.) due to the use of the benzyloxycarbonyl-protecting group. However the acetyl-group offers much less protection to racemisation during methylation under alkaline conditions. Indeed in direct contrast to WO2010107993 (which describes methylation of (R)-N-benzyl-2-(benzyloxycarbonylamino)-3-hydroxy-propionamide), it is found the lowering the temperature during methylation of (R)-2-acetamino-2-N-benzyl-3-hydroxy-propionamide (V) has a very significant benefit by reducing racemisation, however has minimal effect on extent of methylation at the nitrogen groups.

Methylation is typically carried out in a solvent using a methylating agent with a base and phase transfer catalyst. The most preferred methylating agent is dimethyl sulfate, however other methylating agents such as for example methyl iodide or methyl toluenesulfonate or another methyl arylsulfonate or a methyl alkylsulfonate, or trimethylphosphonate may also be used Suitable bases include alkali metal hydroxides or an organolithium compound. Alternatively a quaternary amine may be added as a base, either in combination with another base (such as a metal alkali hydroxide) or alone. In this instance the amine may also act to assist transfer of reactants between the phases. The base and/or methylating reagent may be added all at the beginning of the reaction, or added portion-wise throughout the reaction. Temperature control is important during the reaction and it is preferable to maintain the reaction temperature below 20° C., or more preferably below 10° C. and even more preferably below 5° C. Dichloromethane has been found to work well as a solvent for the reaction, other suitable solvents which do not interfere with the methylation reaction may also be considered, for instance other chlorinated solvents, or ethers such as, for instance, THF or diethoxymethane. Alternatively a mixture of solvents, including water miscible/water immiscible solvent mixtures such as dichloromethane/THF mixtures may be used. Where there are 2 phases in the reaction, for instance solid/liquid or liquid/liquid phases, such as when an aqueous solution of an alkali metal hydroxide (eg a sodium hydroxide solution) is used in the presence of dichloromethane as a solvent, it is necessary to have good mixing to mix the phases. Typically for 2-phase reactions a mixing power input of about 400 W/m$^3$ or greater is preferred. It is preferable to add a phase transfer catalyst to the methylation reaction. Suitable phase transfer catalysts are well known and include quaternary ammonium, sulphonium or phosphonium salts such as tetrabutylammonium salts. Alternatively the addition of a tertiary amine base plus excess methylating agent and base will result in formation of a phase transfer agent in-situ. For instance, methylation of triethylamine with dimethyl sulfate results in formation of a triethylmethylammonium salt. The completion of reaction is preferably when greater than 95% conversion of the starting (R)-2-acetamino-2-N-benzyl-3-hydroxy-propionamide or more preferably greater than 98% conversion of the starting (R)-2-acetamino-2-N-benzyl-3-hydroxy-propionannide has occurred. At completion, it is normal to add ammonia or ammonium hydroxide or other amine to react with and quench any residual un-reacted dimethyl sulfate. At completion of quench, the pH may be adjusted to neutral to assist work-up and enable removal of the base and quench material as salts via aqueous extraction.

Isolation of the lacosamide is performed using standard techniques such as liquid-liquid extraction and crystallisation. Suitable solvents for crystallisation are already well described in the literature and include ethyl acetate and other ester solvents, ethyl acetate/alkane mixtures, toluene or toluene/alcohol mixtures or ether solvent/alcohol mixtures.

Production of (R)-2-acetamino-2-N-benzyl-3-hydroxy-propionamide (V) for use in the invention may be performed in several ways. In U.S. Pat. No. 5,773,475 (and WO 2006037574) it is shown that benzylamine coupling to acetyl-(D)-serine, prior to methylation, using isobutyl chloroformate at –78° C. results in formation of various impurities that must be removed by chromatography. This leads to a complex process with low yield. This is expensive to operate at scale. Therefore, although (R)-2-acetamino-2-N-benzyl-3-hydroxy-propionamide (V) for use in this invention may be produced by direct acetylation of (D)-serine, followed by coupling with benzylamine, this in not preferred. The preferred method for formation of (R)-2-acetamino-2-N-benzyl-3-hydroxy-propionamide (V) starting from starting (D)-serine is protection at the amine group, coupling of the N-protected amino acid with benzylamine followed by de-protection of the amine and acetylation. Scheme 7 shows a potential route for (R)-2-acetamino-2-N-benzyl-3-hydroxy-propionamide (V) preparation using N-(tert-butoxycarbonyl)-('boc-') as a protecting group.

Scheme 7:
Potential route for formation of (R)-2-acetamino-2-N-benzyl-3-hydroxy-propionamide (V) for use in the Invention.
Identification of Intermediates discussed in the text

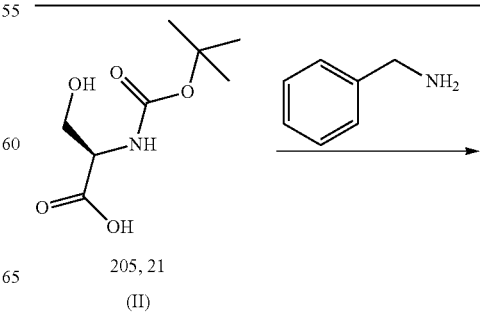

205, 21

(II)

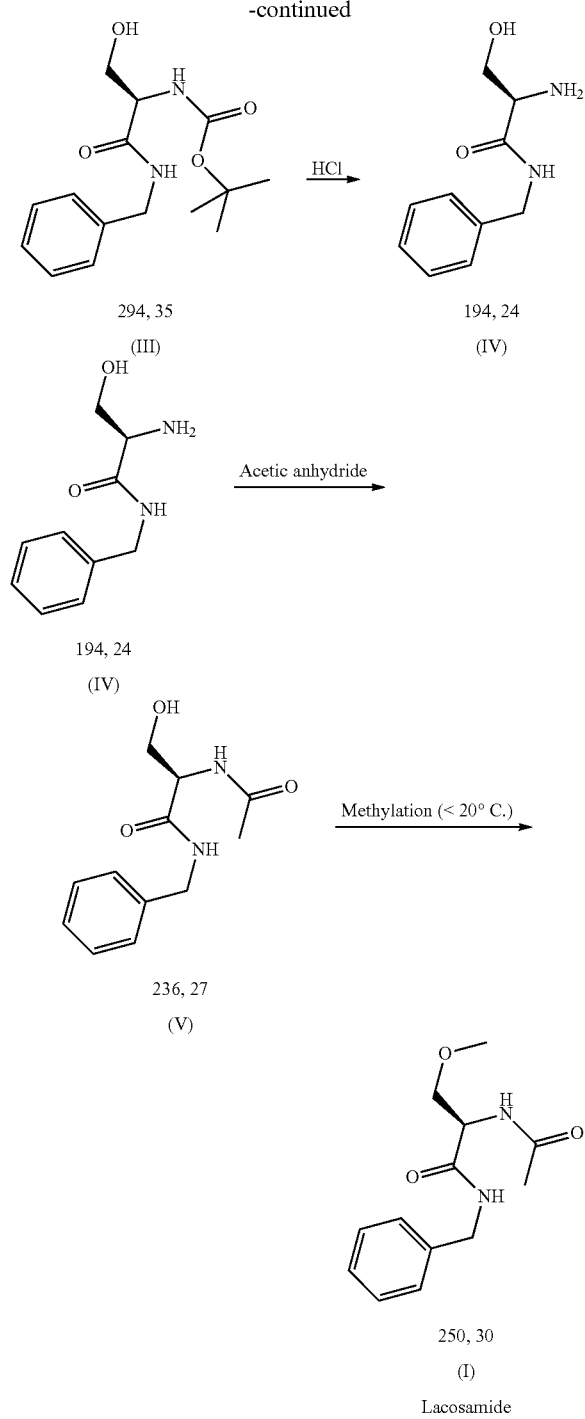

Thus the commercially available N-(tert-butoxycarbonyl)-(D)-serine (boc-(D)-serine, (R)-boc-serine (II)), can be coupled readily with benzylamine without racemisation and with high selectivity using the coupling reagent T3P® (Archimica GmbH, Frankfurt; 2,4,6-tripropyl-2,4,6-trioxo-1,3,5,2,4,6-trioxatriphosphorinane, CAS 68957-94-8). The boc-(D)-serine is dissolved in a suitable solvent. Suitable solvents include, but are not limited to, dichloromethane or an ester such as ethyl acetate or isopropyl acetate. To the reaction mixture is added a base, at typically between 2 and 5 mol equivalents. Common bases for such reactions are triethylamine, diisopropylethylamine, 4-methylmorpholine (N-methylmorpholine) or 2,6-lutidine. 4-methylmorpholine has been found to work well, however other bases may readily be tested for use. Benzylamine is added at preferably 1-1.5 mol equivalents, though larger amounts may also be added. Indeed, as benzylamine is inexpensive, the use of benzylamine as both a base and source of amine for the coupling is possible. The reaction is typically run under cold conditions (2-8° C.), however alternative temperatures are possible. A solution of T3P® in a suitable solvent is then added to the reaction. Suitable solvents for solubilising the T3P® are generally those in which the reaction is carried out and which do not react with the T3P® or interfere with the reaction. In this reaction the most preferred solvents are ethyl acetate and dichloromethane, though other solvents may readily be tested for use in the reaction. At completion of conversion, the reaction is quenched, typically by the addition of water. The pH of the quenched reaction mixture is then adjusted to pH 6-8 so that the amines and reacted T3P® are present as salts. The product may then be isolated using standard liquid-liquid extraction procedures with the product partitioning into the organic phase and the salt by-products remaining in the aqueous phase.

Figure 2:
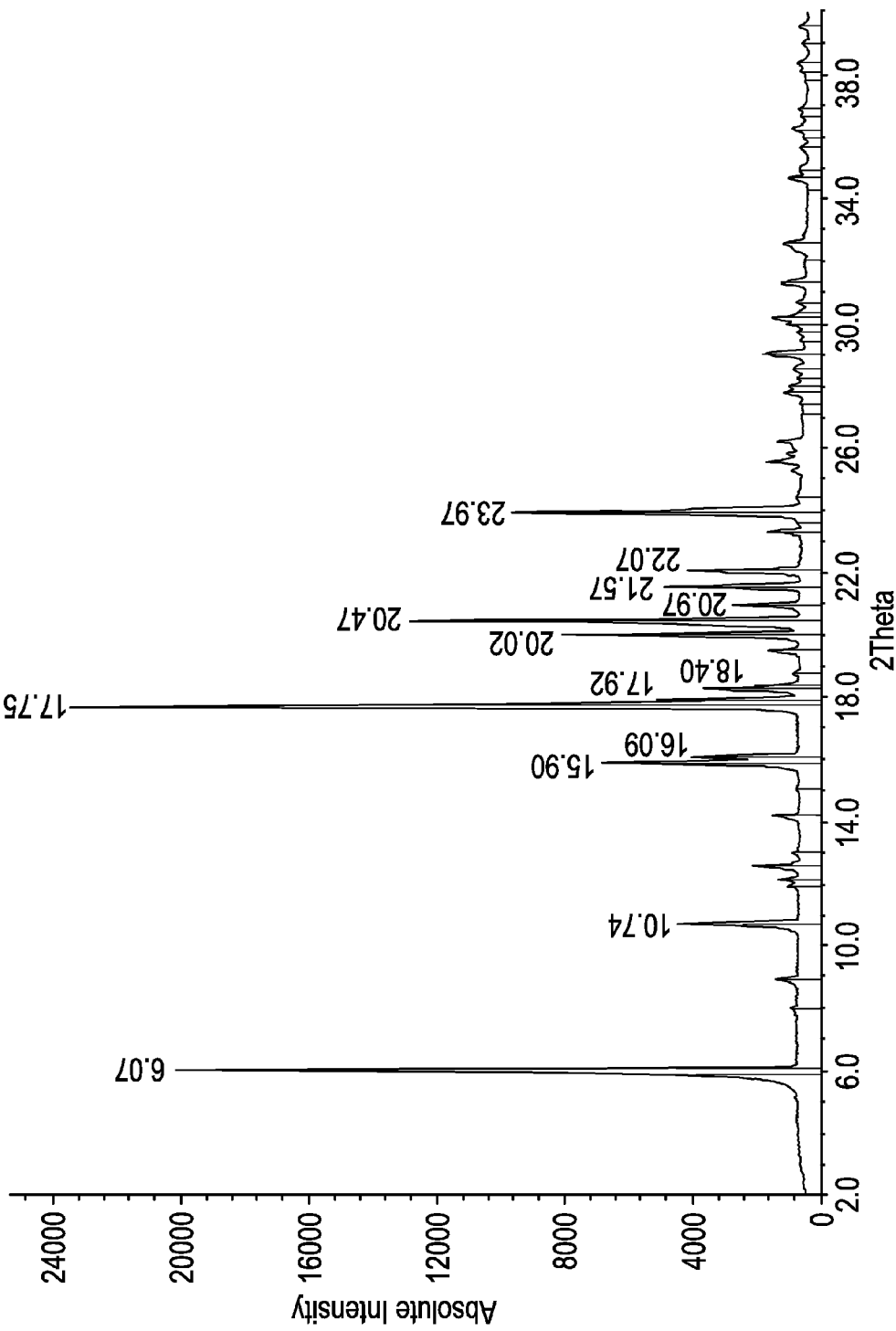
FIG. 2 is an X-ray diffraction pattern of exemplary isolated crystals of (R)-boc-2-amino-N-benzyl-3-hydroxy-propionamide (III) formed in accordance with Example 3.

For higher purity product crystallisation is preferred. Suitable solvents for crystallisation include, but are not limited to, toluene or an ester solvent mixed with an ether. It is expected that any polymorphic crystal form that may be handled for filtration is suitable. The X-ray diffraction pattern of 2 suitable crystal forms are shown in FIGS. 1 and 2 (see Example 2), but these should not be considered limiting and other crystal polymorphic forms may be possible. Alternatively the formed (R)-boc-2-amino-N-benzyl-3-hydroxy-propionamide (III) may be used directly without solid isolation in de-protection/acetylation steps, thereby reducing solids handling. Thus if dichloromethane (or other suitable solvent) is used as a solvent in the coupling reaction the product (III) is already in a solvent suitable for de-protection.

In a further aspect of the invention other common protected derivatives of (D)-serine, besides boc-(D)-serine, eg such as cbz-(D)-serine, trityl-(D)-serine, may also be coupled with benzylamine using T3P® under similar conditions to those employed for benzylamine coupling with boc-(D)-serine. Such intermediates may then be readily reacted through to (R)-2-acetarnino-2-N-benzyl-3-hydroxy-propionarnide (V) by de-protection and acetylation and thus used in the methylation reaction according to this invention.

Although T3P® is the preferred reagent to perform the coupling reaction, other amide coupling reagents such as isobutylchloroformate and dicyclohexylcarbodiimide may also be used.

A further aspect of the invention is the conversion of (R)-boc-2-amino-N-benzyl-3-hydroxy-propionamide (III) to (R)-2-acetamino-2-N-benzyl-3-hydroxy-propionamide (V) in a single reactor without isolation or extraction of intermediate (IV). Due to its relatively good solubility in water, isolation of the de-protected free amine would be problematic; therefore a process in which this intermediate is not required to be isolated is to be preferred. Surprisingly it is found that acetylation of (IV) may be carried out efficiently under aqueous conditions. Thus at the completion of the de-protection reaction with concentrated HCl, no separation of phases, or extraction of intermediate IV ((R)-2-amino-N-benzyl-3-hydroxypropionamide) is required prior to acetylation. At completion of the de-protection, the pH of the reaction is made alkaline by addition of a base such as sodium hydroxide (or other metal hydroxide) or triethylamine (or other tertiary amine base) and the acetylation reaction carried out directly by acetic anhydride addition, without any separation of phases. Despite the lack of an isolation step the reaction goes cleanly with minimal formation of impurities. Additionally by controlling the temperature and operating under cooled conditions (preferably less than 20° C. and more preferably at less than 10° C. and more even preferably at less than 5° C.), racemisation of the chiral centre is minimised, even when using a base such as sodium hydroxide. Acetylation of the hydroxyl group can be minimised by addition of a primary alcohol such as methanol to the reaction mixture. Although (R)-2-acetamino-2-N-benzyl-3-hydroxy-propionamide (V) has some solubility in water, it is found that good isolation can be achieved by crystallising from a 2-phase reaction mixture without extraction.

Figure 3:
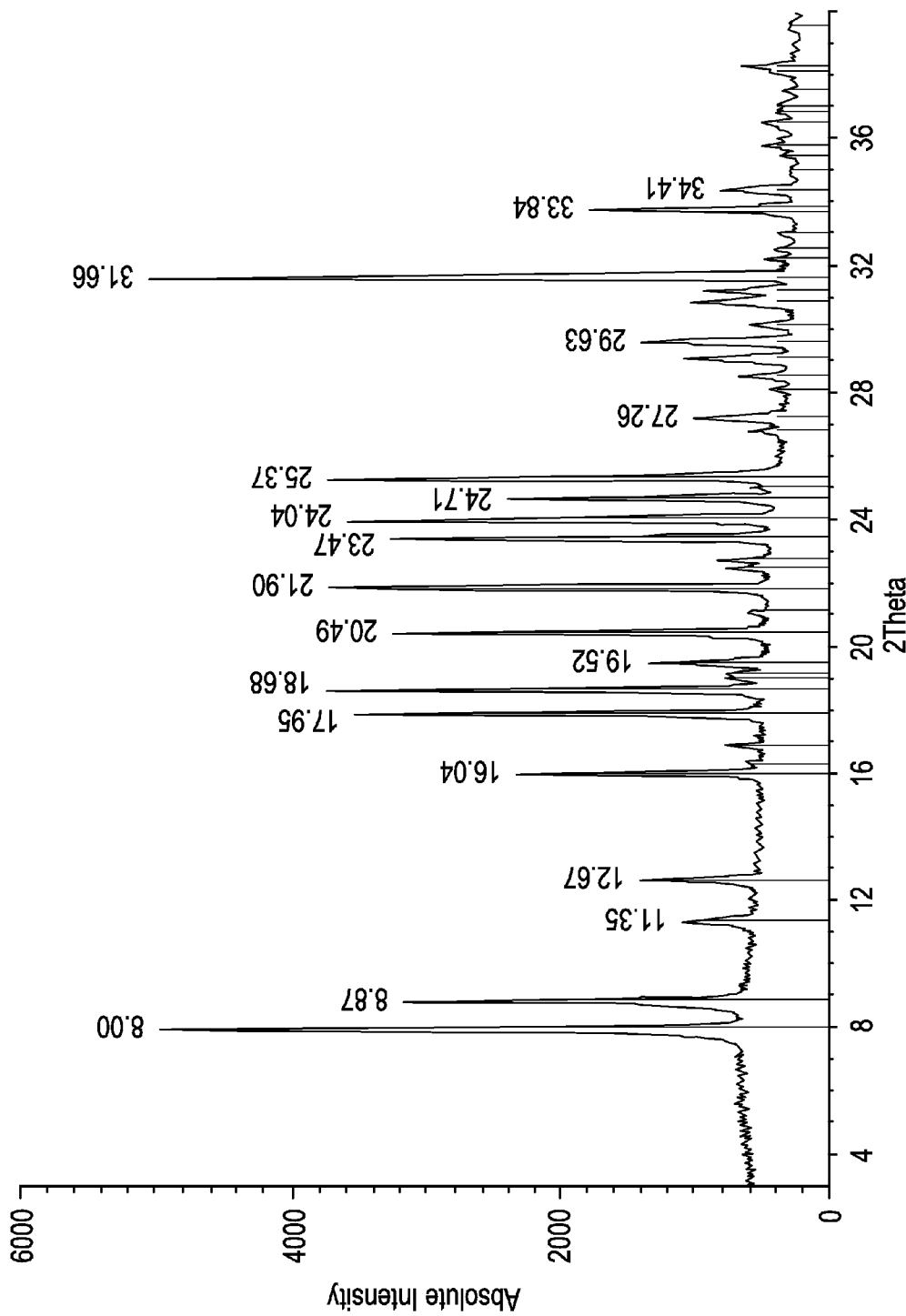
FIG. 3 is an X-ray diffraction pattern of exemplary isolated crystals of (R)-2-acetamido-N-benzyl-3-hydroxy-propionamide (V) formed in accordance with Example 5.
Figure 4:
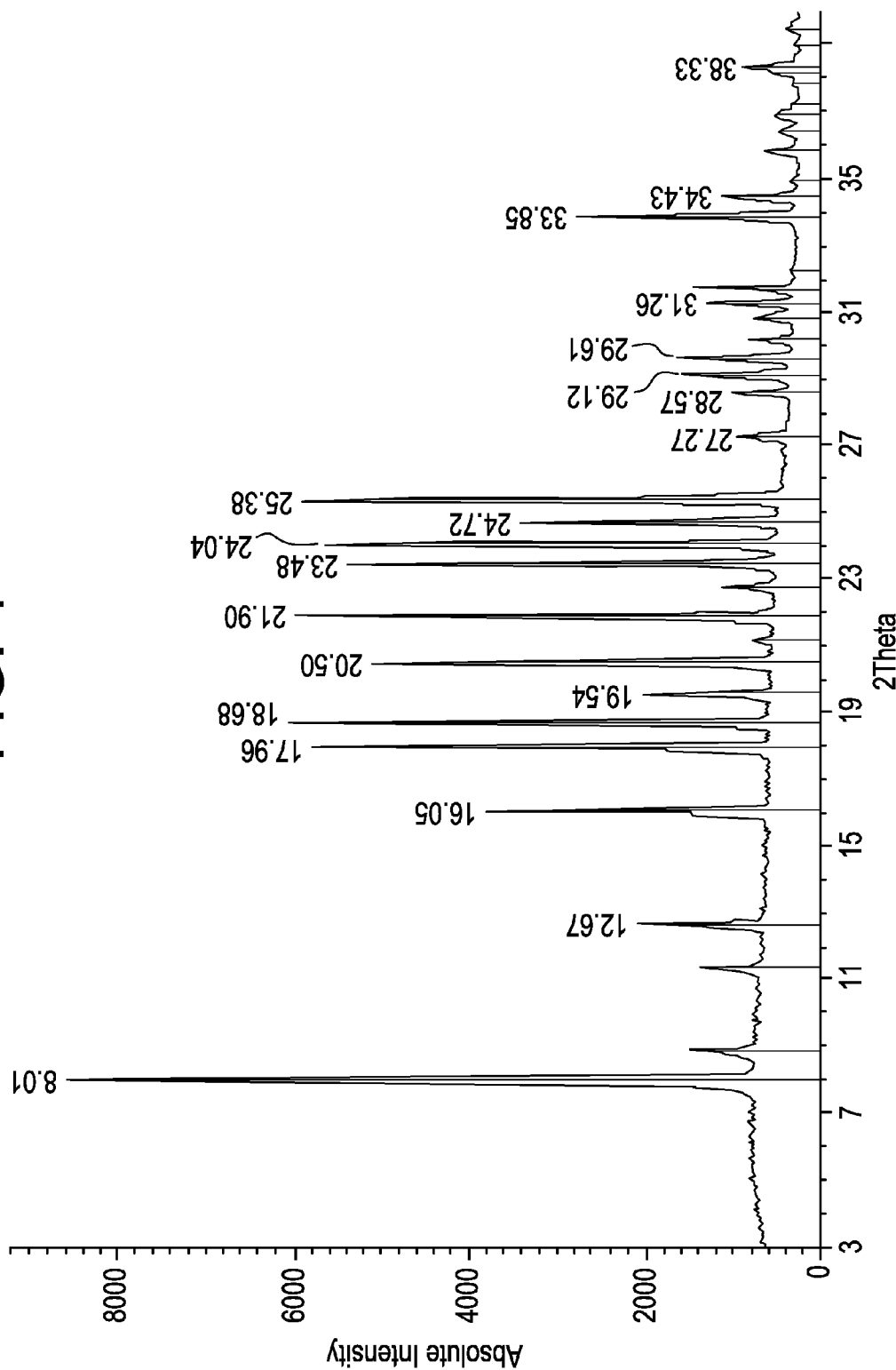
FIG. 4 is an X-ray diffraction pattern of exemplary isolated crystals of (R)-2-acetamido-N-benzyl-3-hydroxy-propionamide (V) formed in accordance with Example 6.

Residual salts are readily removed by using cold water wash. Alternatively the product can be isolated by stripping the organic solvent completely and crystallising from an aqueous solution. Enhancement of optical purity is possible during crystallisation. Thus (R)-2-acetamino-2-N-benzyl-3-hydroxy-propionamide (V) with an ee of 98% (and potentially even lower) may readily be crystallised to an ee of greater than 99.5%. It is expected that any polymorphic crystal form that may be handled for filtration is suitable. The X-ray diffraction pattern of 2 suitable crystal forms are shown in FIGS. 3 and 4 (see Example 4), but these should not be considered limiting and other crystal polymorphic forms may be possible. The formed (R)-2-acetamino-2-N-benzyl-3-hydroxy-propionamide (V) may then be used in the methylation reaction according to the invention.

ee is enantiomeric excess and is calculated by determining the percentage of each separate enantiomer of a given chiral compound, such that the sum of the (R) and (S) enantiomers is 100%, and subtracting one from the other. For the purposes of this invention the ee of the indicated enantiomer is at least equal to 90% or greater unless otherwise indicated.

EXAMPLES 1. (R)-boc-2-amino-N-benzyl-3-hydroxy-propionamide (III)

In a 4 L flask with overhead stirrer, thermometer, dropping funnel and under nitrogen were combined 150 g boc-(D)-serine (0.731 mol) (ee>99%), 1.5 kg ethyl acetate and 221.5 g 4-methylmorpholine (2.19 mol). The reactor was cooled in an ice bath to 4-8° C. and 129.4 g benzylamine (1.24 mol) slowly added. After complete addition a thick slurry was obtained. 525 g of T3P® in ethyl acetate (2,4,6-tri-n-propyl-2,4,6-trioxo-1,3,5,2,4,6-trioxatriphosphorinane as a 50% w/w solution in ethyl acetate, 0.826 mol) were slowly added, maintaining the temperature below 15° C. The mixture was cooled and stirred on ice at 4-8° C. for 1.5 hours, then at 25° C. for 2 hours. The reaction was quenched by the addition of 400 ml water and stirred for a further 30 minutes. The phases were separated and the aqueous phase re-extracted with 750 ml ethyl acetate. The combined organic phases were washed 200 ml water, adjusted to pH 6 with 37% HCl, then washed a second time with 150 ml water. The ethyl acetate was stripped and exchanged to toluene. The product was crystallised from 1 kg toluene by cooling to 4-8° C. The product was filtered and washed with 2×100 ml toluene. After drying under vacuum at 40° C., 153.8 g (yield 71.5%) (R)-boc-2-amino-N-benzyl-3-hydroxy-propionamide (III) were obtained. HPLC purity >99%, ee 99%, $^1$H NMR (400 MHz, CDCl$_3$): δ=1.42 (s, 9 H), 3.12 (br, 1 H), 3.65-3.69 (m, 1 H), 4.12-4.18 (m, 2 H), 4.36-4.53 (m, 2 H), 5.62 (d, J=6.0, 1 H), 7.08 (br, 1 H), 7.21-7.36 (m, 5 H).

2. (R)-boc-2-amino-N-benzyl-3-hydroxy-propionamide (III)

In a 4 L flask with overhead stirrer, thermometer, dropping funnel and under nitrogen were combined 150 g boc-(D)-serine (0.731 mol) (ee>99%), 2.13 kg dichloromethane and 221.5 g 4-methylmorpholine (2.19 mol). The reactor was cooled in an ice bath to 4-8° C. and 129.4 g benzylamine (1.24 mol) slowly added. After complete addition, a slurry was obtained. 516 g of T3P® in dichloromethane (2,4,6-tri-n-propyl-2,4,6-trioxo-1,3,5,2,4,6-trioxatriphosphorinane as a 50% w/w solution in dichloromethane, 0.811 mol) were slowly added, maintaining the temperature below 8° C. The mixture was cooled and stirred on ice at 4-8° C. for 2 hours. The reaction was quenched by the addition of 400 ml water, brought to room temperature and stirred for a further 30 minutes. The phases were separated and the aqueous phase re-extracted with 750 ml dichloromethane. The combined organic phases were washed 140 ml water, adjusted to pH 6 with 10% HCl and stirred for a further 1 hour at room temperature. The phases were separated and the organic phase re-washed with 200 ml water. The dichloromethane was stripped and exchanged to toluene. The product was crystallised from 1 kg toluene by cooling to room temperature over 3 hours, then standing in the fridge overnight. The product was filtered and washed with 2×150 ml toluene. After drying under vacuum at 40° C., 165 g (yield 76.5%) (R)-boc-2-amino-N-benzyl-3-hydroxy-propionamide (III) were obtained. HPLC purity >99%, ee >99%. The X-ray diffraction pattern of the isolated crystals is shown in FIG. 1. X-ray diffraction pattern of (R)-boc-2-amino-N-benzyl-3-hydroxy-propionamide (III). Major peaks observed at around Theta values of 5.7, 6.0 9.2, 10.8, 12.4, 17.6, 18.2, 18.7, 19.7, 20.4 and 22.3.

3. (R)-boc-2-amino-N-benzyl-3-hydroxy-propionamide (III)

In a 12 L reactor, a similar reaction to that described in 2 was carried out except that 500 g boc-(D)-serine was used and proportions of reactants were increased proportionately. At the completion, the reaction was quenched by the addition of 1330 ml water, stirred for 1 hour at 5° C., the stirrer was then turned off allowing the phases to separate and the reaction was left at 5° C. over weekend. The phases were then separated and the aqueous phase re-extracted with 2.5 L dichloromethane. The organic phases were combined and washed with 470 ml water at 20° C. 10% HCl was added to bring the pH to 6 and stirred for a further 1 hour at room temperature. The phases were separated and the organic phase re-washed with 670 ml water. The dichloromethane was stripped and exchanged to toluene. The product was crystallised from 3.3 kg toluene by cooling with mixing to room temperature over 6 hours, holding at room temperature for 9 hours and then cooling on ice for 6 hours. The product was filtered and washed with 2×500 ml toluene. After drying under vacuum at 40° C., 531 g (yield 74%) (R)-boc-2-amino-N-benzyl-3-hydroxy-propionamide (III) were obtained. HPLC purity >99%, ee >99%. The X-ray diffraction pattern of the isolated crystals is shown in FIG. 2. X-ray diffraction pattern of (R)-boc-2-amino-N-benzyl-3-hydroxy-propionamide (III). Major peaks observed at around Theta values of 6.1, 10.8, 15.9, 16.1, 17.8, 20.0, 20.5, 21.6, 22.1 and 24.0.

Both crystal forms isolated in Examples 2 and 3 are considered suitable for use in the invention.

4.
(R)-2-acetamido-N-benzyl-3-hydroxypropionamide
(V)

In a 2 L flask with overhead stirrer, condenser, thermometer and dropping funnel were combined 140 g (R)-boc-2-amino-N-benzyl-3-hydroxy-propionamide (III) and 700 ml dichloromethane. To this was carefully added 167 g, 37% w/w HCl and the reaction mixture was stirred at room temperature for 90 minutes, to remove the 'boc' protecting group. The reaction mixture was then put on ice and 25 ml methanol and 234 g of triethylamine added, maintaining the temperature below 8° C. To the reaction was then added 53 g acetic acid anhydride and the reaction stirred for 30 minutes on ice. The reaction was then warmed to room temperature and stirred for a further hour. 67 g of 37% HCl were added to bring the pH to 6.3 and the mixture stripped at 40-50° C. under vacuum to remove 950 g solvent plus water. Ethyl acetate was added to bring the mass to 420 g and the product crystallised by cooling overnight in the fridge. The product was filtered and washed with 88 ml water, followed by 88 ml ethyl acetate to give a product (ee>99% by chiral HPLC).

5.
(R)-2-acetamido-N-benzyl-3-hydroxypropionamide
(V)

In a 2 L flask with overhead stirrer, condenser, thermometer and dropping funnel were combined 140 g (R)-boc-2-amino-N-benzyl-3-hydroxy-propionamide (III) (prepared as described in Example 2) and 840 ml dichloromethane. To this was carefully added 167 g, 37% w/w HCl and the reaction mixture was stirred at room temperature for 90 minutes, to remove the 'boc' protecting group. The reaction mixture was then put on ice and 25 ml methanol and 274 g 33% sodium hydroxide added, maintaining the temperature below 8° C. To the reaction was then added 58 g acetic acid anhydride and the reaction stirred for 30 minutes on ice. A further 10 ml methanol, 7 g 33% sodium hydroxide and 28 g acetic acid anhydride was then added and the reaction stirred for a further 30 minutes. The pH was 6.7. The mixture was then slowly heated to remove the dichloromethane and then to 75° C. When no more solvent distilled, water was added to bring the mixture mass to 1.1 kg and heated until every thing was in solution. The solution was then slowly cooled with stirring to 5° C. The crystals were filtered, washed 2 times with 90 ml water and dried at 40-50° C. under vacuum with a stream of nitrogen. Isolated mass=100.3 g, 89% yield, ee >99.5%, HPLC purity 99%, sodium chloride plus sodium acetate content 1.7%, water content 0.12%. The X-ray diffraction pattern of the isolated crystals is shown in FIG. 3: X-ray diffraction pattern of (R)-2-acetamido-N-benzyl-3-hydroxy-propionamide (V). Major peaks observed at around Theta values of 8.0, 8.9, 16.0, 18.0, 18.7, 20.5 2.9, 23.5, 24.0, 24.7 25.4, 31.7 and 33.8.

6.
(R)-2-acetamido-N-benzyl-3-hydroxypropionamide
(V)

In a similar reaction to that described in Example 5, the isolated solid was re-crystallised from 750 ml water and washed 2 times with 80 ml of water to give 104 g after drying (solid yield 92.5%) ee>99.5%, HPLC purity 99%, sodium chloride plus sodium acetate content 3.8%, water content 0.16%. The X-ray diffraction pattern of the isolated crystals is shown in FIG. 4: X-ray diffraction pattern of (R)-2-acetamido-N-benzyl-3-hydroxy-propionamide (V) Major peaks observed at around Theta values of 8.0, 12.7, 16.0, 18.0, 18.7, 20.5, 21.9, 23.5, 24.0 24.7 25.4 and 33.8.

Whilst both crystal forms shown in FIGS. 3 and 4 are considered suitable for use, that shown in FIG. 4 is preferred as being easier to handle.

7. Lacosamide (I) ((R)-2-acetamido-N-benzyl-3-methoxypropionamide)

(a) In a 0.25 L jacketed flask with overhead stirrer, thermometer, dropping funnel were combined 4.7 g (20 mmole) (R)-2-acetamido-N-benzyl-3-hydroxypropionamide (V) (prepared by the method described in Example 5 and 44 ml dichloromethane). The reactor was adjusted to 22° C., then 0.3 g tetrabutylammonium bisulfate, 1 g triethylamine and 5.5 g (44 mmole) dimethyl sulfate were added. A total of 4,5 g of a 33% solution of sodium hydroxide in water was then added in 5 pulses over 4 hours. After 18 hours a sample showed 88% formation of lacosamide, 3% residual (R)-2-acetamido-N-benzyl-3-hydroxypropionamide starter and 9% of the over-methylated impurities (methylated at 1 of the nitrogen's and at the hydroxyl function). The reaction was quenched by the addition of 2,4 g ammonium chloride in 30 ml water plus 12 g of a 25% ammonia solution in water. After 4 hours stirring, the pH was adjusted to 7-8 by the drop-wise addition of 37% HCl in water (ensuring the temperature was maintained below 25° C.). The organic phase was separated, washed with water and analysed The lacosamide had an ee of 89%.

After exchanging the solvent to ethyl acetate and crystallisation, the crystals had an ee of >99.5%. The mother liquor showed an ee of 66%. Thus approximately of 32% of the formed and extracted lacosarnide was lost on crystallisation. Overall yield of lacosamide after drying was 54%. Thus although good quality material can be produced from such low ee material significant amount of formed lacosamide is lost.

(b) A similar reaction was carried out to Example 7 (a) except that the temperature was maintained at 5° C. throughout the reaction. After 26 hours a sample showed 3% residual (R)-2-acetamido-N-benzyl-3-hydroxypropionamide starter and 9% of the over-methylated impurities—a similar profile to the reaction at 22° C. The ee of the formed lacosamide however was 99%. This is a significant improvement over that achieved at the higher temperature, but with otherwise little effect on the impurity profile.

8. Lacosamide (I) ((R)-2-acetamido-N-benzyl-3-methoxypropionamide)

In a 0.8 L jacketed flask with overhead stirrer, thermometer, dropping funnel were combined 28.4 g (R)-2-acetamido-N-benzyl-3-hydroxypropionamide (V) (prepared using the method described in Example 5) and 264 ml dichloromethane. The reactor was cooled to 3° C., then 1.6 g tetrabutylammonium bisulfate, 6.1 g triethylamine and 33.3 g dimethyl sulfate were added. A total of 27.2 g of a 33% solution of sodium hydroxide in water was then added in 5 pulses over 4 hours. After 28 hours a sample showed 88% formation of lacosamide, 4% residual (R)-2-acetamido-N-benzyl-3-hydroxypropionamide starter and 8% of the over methylated impurities. The reaction was quenched by the addition of 14.3 g ammonium chloride in 30 ml water plus 71.8 g of a 25% ammonia solution in water. After stirring overnight at 3° C., the pH was adjusted to 7.4 by the drop-wise addition of 37% HCl in water at room temperature. 50 ml further water was added to dissolve salts. The phases were separated and the aqueous re-extracted with 140 ml dichloromethane. The combined organic phases were washed 2 times with 42 ml water. The solvent was exchanged for ethyl acetate and the lacosamide crystallised from 280 ml ethyl acetate, by warming until all solid was in solution, then slowly cooling to 5° C. The product was filtered, washed 2 times with ethyl acetate and dried to give 19.7 g solid (>99.6% HPLC purity, >99.9% ee), yield 65%—a very significant improvement over the yield obtained in Example 7(a).

That which is claimed:

1. A method for producing (R)-2-acetamido-N-benzyl-3-methoxypropionamide comprising methylating (R)-2-acetamino-2-N-benzyl-3-hydroxy-propionamide (V), wherein the methylation is carried out at a temperature below 20° C.

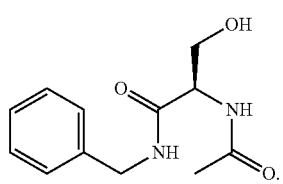

(V)

2. A process according to claim 1, wherein the temperature during methylation is maintained below 10° C.

3. A process according to claim 1, wherein the temperature during methylation is maintained below 5° C.

4. A process according to claim 1, further comprising dimethyl sulfate as a methylation agent.

5. A process according to claim 1, further comprising methyl iodide, methyl toluenesulfonate or another methyl arylsulfonate, a methyl alkylsulfonate, or trimethylphosphonate as a methylation agent.

6. A process according to claim 1, wherein the ee of the isolated (R)-2-acetamino-2-N-benzyl-3-methoxy-propionamide is greater than or equal to 97%.

7. A process according to claim 1, wherein the ee of the isolated (R)-2-acetamino-2-N-benzyl-3-methoxy-propionamide is greater than or equal to 99%.

8. A process according to claim 1, wherein a phase transfer catalyst is present during methylation.

9. A process according to claim 1, wherein an alkali metal hydroxide base is present.

10. A process according to claim 1, wherein (R)-2-acetamino-2-N-benzyl-3-hydroxy-propionamide (V) is produced via de-protection and acetylation of (R)-boc-2-amino-N-benzyl-3-hydroxy-propionamide (III) and intermediate (R)-2-amino-N-benzyl-3-hydroxy-propionamide (IV) is not isolated.

11. A process according to claim 10, wherein (R)-N-(tert-butoxycarbonyl)-2-amino-N-benzyl-3-hydroxy-propionamide (III) is produced by coupling (R)-N-(tert-butoxycarbonyl)-serine and benzylamine using 2,4,6-tripropyl-2,4,6-trioxo-1,3,5,2,4,6-trioxatriphosphorinane as a coupling reagent in the presence of a base.

* * * * *